(12) United States Patent
Belcheva et al.

(10) Patent No.: US 8,969,485 B2
(45) Date of Patent: Mar. 3, 2015

(54) SURFACE INDUCED RING-OPENING POLYMERIZATION AND MEDICAL DEVICES FORMED THEREFROM

(71) Applicant: Covidien LP, Mansfield, MA (US)

(72) Inventors: Nadya D. Belcheva, Essex Junction, VT (US); Norman Aminuddin, Madison, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/934,507

(22) Filed: Jul. 3, 2013

(65) Prior Publication Data
US 2013/0296932 A1 Nov. 7, 2013

Related U.S. Application Data

(62) Division of application No. 13/208,525, filed on Aug. 12, 2011, now Pat. No. 8,501,875.

(60) Provisional application No. 61/407,610, filed on Oct. 28, 2010.

(51) Int. Cl.
| | | |
|---|---|---|
| C08G 63/91 | (2006.01) | |
| C09D 167/04 | (2006.01) | |
| C08G 63/06 | (2006.01) | |
| C08G 63/78 | (2006.01) | |
| A61L 17/14 | (2006.01) | |

(52) U.S. Cl.
CPC .............. *C09D 167/04* (2013.01); *C08G 63/06* (2013.01); *C08G 63/78* (2013.01); *A61L 17/145* (2013.01)
USPC ............ 525/411; 525/410; 525/415; 525/450

(58) Field of Classification Search
CPC ........ C08G 63/12; C08G 63/16; C08F 16/06; C08L 67/02; C08L 29/04
USPC ............................ 525/56, 165, 174, 437, 445
See application file for complete search history.

(56) References Cited

U.S. PATENT DOCUMENTS

| | | | |
|---|---|---|---|
| 4,080,491 A | 3/1978 | Kobayashi et al. | |
| 4,529,788 A | 7/1985 | Asami et al. | |
| 4,902,515 A | 2/1990 | Loomis et al. | |
| 5,288,841 A | 2/1994 | Bellis et al. | |
| 5,412,067 A | 5/1995 | Shinoda et al. | |
| 5,484,882 A | 1/1996 | Takada et al. | |
| 5,521,278 A | 5/1996 | O'Brien et al. | |
| 5,611,983 A | 3/1997 | Ma et al. | |
| 5,665,831 A | 9/1997 | Neuenschwander et al. | |
| 5,889,127 A | 3/1999 | Iiyama et al. | |
| 5,981,743 A | 11/1999 | Gross et al. | |
| 5,998,552 A | 12/1999 | Gruber et al. | |
| 6,277,951 B1 | 8/2001 | Gruber et al. | |
| 6,417,266 B1 | 7/2002 | Terado et al. | |
| 6,624,321 B2 | 9/2003 | Denninger et al. | |
| 6,670,428 B1 | 12/2003 | Yasumura et al. | |
| 6,800,663 B2 | 10/2004 | Asgarzadeh et al. | |
| 6,864,351 B2 | 3/2005 | Sakane et al. | |
| 7,094,862 B2 | 8/2006 | Cazaux et al. | |
| 7,538,178 B2 | 5/2009 | Sato et al. | |
| 7,538,179 B2 | 5/2009 | Sato et al. | |
| 2001/0053866 A1 | 12/2001 | Denninger et al. | |
| 2003/0097026 A1 | 5/2003 | Denninger et al. | |
| 2003/0187181 A1 | 10/2003 | Sakane et al. | |
| 2005/0080226 A1 | 4/2005 | Watanabe | |
| 2005/0096481 A1 | 5/2005 | Hildebrandt et al. | |
| 2005/0171299 A1 | 8/2005 | Shalaby | |
| 2006/0004183 A1 | 1/2006 | Sato et al. | |
| 2006/0235113 A1 | 10/2006 | Dorgan et al. | |
| 2007/0043434 A1 | 2/2007 | Meerkin et al. | |
| 2007/0073032 A1 | 3/2007 | Sato et al. | |
| 2007/0073033 A1 | 3/2007 | Sato et al. | |
| 2007/0190333 A1 | 8/2007 | Matsugi et al. | |
| 2008/0014240 A1 | 1/2008 | Gale et al. | |
| 2008/0118546 A1 | 5/2008 | Thatcher et al. | |
| 2008/0214842 A1 | 9/2008 | Ogawa et al. | |

FOREIGN PATENT DOCUMENTS

WO      2009062222 A1      5/2009

OTHER PUBLICATIONS

Chen, L., et al.; Carbohydrate Polymers, 2005, p. 103-109.*
BASF; Epsilon-Caprolactone Technical Data Sheet, 2009.*
Liu, P., et al.; Carbohydrate Polymers, 2009, p. 250-253.*
International Search Report from European Application No. 12173538.5 dated Aug. 13, 2013.
Ikada, Y.; Tsuji, H.; Macromolecular Rapid Communications, 2000, vol. 21, pp. 117-132.
Jayasekara, R., et al.; Journal of Polymers and the Environment, 2005, vol. 13, No. 3, pp. 231-251.
Database WPI Wee 200905, Thomson Scientific, London, GB; AN 2009-A95763; XP002670164 & KR 100 821 464 B1 (Univ Hannam Inst Ind Acad Coop) Apr. 11, 2008.
European Search Report corresponding to European Application No. 11250779.3-2102; completed on Feb. 23, 2012 and mailed Mar. 8, 2012. (3 Pages).

* cited by examiner

*Primary Examiner* — Robert Jones, Jr.

(57) ABSTRACT

The present disclosure relates to coated biodegradable materials having a reduced amount of residual catalysts and methods thereof.

19 Claims, 2 Drawing Sheets

SURFACE INDUCED RING-OPENING POLYMERIZATION AND MEDICAL DEVICES FORMED THEREFROM

CROSS-REFERENCE TO RELATED APPLICATION

The present application is Divisional Application claiming the benefit of and priority to U.S. patent application Ser. No. 13/208,525, filed Aug. 12, 2011, which claims the benefit of and priority to U.S. Provisional Application Ser. No. 61/407,610, filed on Oct. 28, 2010, the entire disclosures of which are incorporated herein by reference.

BACKGROUND

1. Technical Field

The present disclosure relates to methods of inducing ring-opening polymerization on a surface of biodegradable polymeric materials and the medical devices formed therefrom.

2. Background of Related Art

Polyesters represent a commercially important class of polymers. One route to forming polyesters is via ring-opening polymerization of cyclic esters. For example, $\epsilon$-caprolactone can by polymerized to polycaprolactone, which is widely used as a biocompatible material for the fabrication of implantable devices. Known ring-opening polymerization methods may require the addition of a catalyst to drive the reaction. Such methods often produce polymers which include residual amounts of the catalysts. That is to say, not all of the catalyst provided to drive the polymerization reaction may be utilized thereby being left within the polymeric material. The residual or excess catalyst is an impurity which may make decrease the strength of the polymeric material. In addition, upon degradation, the release of the residual catalyst from the polymeric material may be toxic to the environment and/or the patient in which the polymeric material is implanted. Therefore, a need exists for improving polymerization processes which produce biodegradable polymeric materials including reduced amounts of impurities and/or reduced amount of residual catalysts.

SUMMARY

Accordingly, methods are described herein for reducing the amount of a residual catalyst from a biodegradable polymeric material. The methods include: providing a container which includes at least one monomer capable of polymerizing via cationic ring-opening polymerization and a biodegradable polymeric material containing an amount of a residual catalyst; and, heating the container above the glass transition temperature of the biodegradable polymeric material and below the crystallization temperature of the biodegradable polymeric material for a period of time sufficient to reduce the amount of residual catalyst in the biodegradable polymeric material.

In some methods, the container may include a heating means. In other embodiments, the container may be positioned within a separate heating means, such as an oven.

In certain embodiments, methods of grafting a biodegradable coating onto a surface of a biodegradable polymeric material are described. The methods include: providing a container which includes at least one monomer capable of polymerizing via cationic ring-opening polymerization, positioning a biodegradable polymeric material containing an amount of a residual catalyst in the container, and placing the container with the biodegradable polymeric material in an oven for a period of time, wherein the oven is heated above the glass transition temperature and below the crystallization temperature of the biodegradable polymeric material. The container may be heated for a period of time sufficient to reduce the amount of residual catalyst in the biodegradable polymeric material and/or provide the substrate with a biodegradable coating grafted to a surface of the substrate.

In still other embodiments, methods of inducing ring-opening polymerization of an aliphatic cyclic ester monomer on a surface of a medical device are also described. Such methods include: providing a closed container which includes an aliphatic cyclic ester monomer and a medical device made from a cyclic aliphatic ester; and, heating the closed container to at least a glass transition temperature of the cyclic aliphatic ester of the medical device and below the crystallization temperature of the cyclic aliphatic ester of the medical device to induce ring-opening polymerization of the aliphatic cyclic ester monomer along the surface of the medical device. The medical device may include a first amount of residual catalyst prior to being heated and a second different amount of residual catalyst after being heated, wherein the first amount is higher than the second amount of residual catalyst.

The coated biodegradable polymeric materials containing a reduced amount of residual catalyst are also described herein. In embodiments, the biodegradable polymeric materials may be in a pellet format. In some embodiments, the biodegradable polymeric materials may be in the form of an implantable medical device. The biodegradable polymeric materials include a substrate containing a reduced amount of residual catalyst, and a biodegradable coating positioned on at least a portion of the substrate, wherein the coating is grafted via interpenetrating mechanisms through a surface of the substrate.

BRIEF DESCRIPTION OF THE DRAWINGS

The accompanying drawing, which is incorporated in and constitutes a part of this specification, illustrates embodiments of the disclosure and, together with a general description of the disclosure given above, and the detailed description of the embodiments given below, serves to explain the principles of the disclosure.

DETAILED DESCRIPTION

Figure 1A:
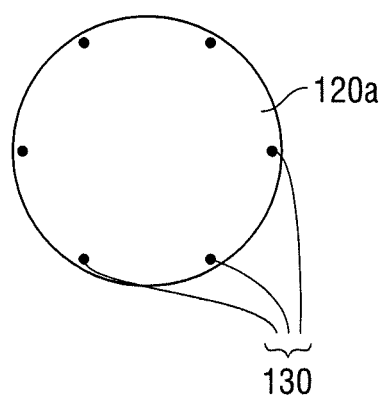
FIG. 1A shows a biodegradable polymeric material prior to the methods described herein.

The present disclosure describes methods of inducing ring-opening polymerization on the surface of a biodegradable polymeric material. Such methods provide a coating on the biodegradable polymeric materials. In addition, such methods reduce the amount of residual catalysts in the biodegradable polymeric material thereby purifying and strengthening the material.

Unlike other known coating processes, the methods described herein do not require the use of a solvent to form the coating and as a result the biodegradable polymeric materials may include a coating made from a "friendlier" polymer, i.e., less toxic to the patient and/or environment, without compromising the mechanical strength of the biodegradable polymeric material. Such methods provide coated biodegradable polymeric materials wherein the coating is physically grafted (i.e., interpenetrating mechanisms) through a surface to a depth in the biodegradable polymeric material. Such coatings may improve the mechanical strength of the biodegradable polymeric material. The coatings may be continuous or discontinuous along the polymeric material.

Initially, at least one monomer capable of polymerizing via ring-opening polymerization and/or at least one biodegradable polymeric material including a first amount of residual catalyst may be positioned within a container, i.e., reaction vessel. It is envisioned that the monomer and the biodegradable polymeric material may be positioned within the container in any order. The container may then be sealed and the contents positioned within the container may be heated above the glass transition temperature and below the crystallization temperature of the biodegradable polymeric material.

The polymeric materials described herein may include amorphous and crystalline portions. Heating a polymeric material above its respective glass transition temperature will reversibly change the amorphous portions of the polymeric material from a hard, glassy, or brittle condition to a flexible or elastomeric condition. Conversely, cooling the polymeric material below its respective glass transition temperature will reversibly change the amorphous portions of the polymeric material from a flexible or elastomeric condition to a hard, glassy, or brittle condition. The glass transition temperature for each polymeric material may be different.

The crystallization temperature represents the temperature at which the crystalline portions of a polymeric material begin to become organized crystals. The crystallization temperature is often higher than the glass transition temperature of a polymeric material and lower than the melting temperature of the polymeric material. Unlike the melting temperature, as the polymeric material approaches the crystallization temperature, the crystalline portions of the polymeric materials will begin to organize as crystals thereby producing an exothermic reaction or providing heat to the area surrounding the polymeric material. It is envisioned that this additional heat or energy may further drive the ring-opening polymerization processes described herein.

Heating of the biodegradable polymeric material above the glass transition temperature and below the crystallization temperature of the polymeric material allows the amorphous portions of the biodegradable polymeric material to soften, creating less dense regions, such as pores in the surface of the biodegradable polymeric material. In embodiments, the softening and/or pores of the biodegradable polymeric material My allow the residual catalyst to be released to a surface of the biodegradable material and interact with the monomer positioned in the container. In certain embodiments, the softening and/or pores of the biodegradable polymeric material allows the monomer to enter the surface of the biodegradable material and interact with the residual catalyst positioned in the polymer. It is envisioned that the residual catalyst will polymerize the monomer via ring-opening polymerization along the surface of the material thereby forming a coating layer on the material. In embodiments, the monomer may interact with the residual catalyst and penetrate a certain depth below the surface of the material creating a grafted coating via interpenetrating mechanisms through a surface of the polymeric material.

In some embodiments, an aliphatic cyclic ester monomer, such as $\epsilon$-caprolactone, may be placed in the container with an implantable medical device made from polylactide which includes a first amount of a residual catalyst such as stannous octoate. In embodiments, the monomer may not include a solvent. The temperature inside the container may be heated to a temperature slightly above the glass transition temperature and below the crystallization temperature of the polylactide suture material, i.e., to between about 70° C. and about 80° C., to soften the amorphous phase of the polylactide suture material. Softening of the amorphous phase of the suture material may subsequently lead to enhanced diffusion of the residual catalyst out of the suture material, as well as enhance diffusion of the monomer into the surface layer of the suture material. The monomer and the residual catalyst may interact to form a poly(caprolactone) coating on the surface of polylactide suture material and the polylactide suture material will include a second amount of residual catalyst which is less than the first amount of residual catalyst. More specifically, the monomer undergoes ring-opening polymerization on the surface of the medical device, the reaction driven by the stannous octoate.

The container or reaction vessel includes a sealable door through which one or more monomers and/or biodegradable polymeric materials may pass to be placed or removed from the reaction vessel. While the biodegradable polymeric materials may be placed into the reaction vessel in any manner or position, the greater the surface area of the biodegradable polymeric materials that is accessible to the monomer, the more likely the monomer is to come into contact with residual catalyst and form a grafted coating on the biodegradable polymeric materials. In some embodiments, a rack adapted to hold the one or more biodegradable polymeric materials may be placed within the reaction vessel. For example, in some embodiments, biodegradable polymeric materials such as sutures may be wound on a spool or a rack and placed within the reaction vessel.

The interior of reaction vessel can be advantageously made from or lined with a material that is non-reactive with the biodegradable polymeric materials and/or the monomer. Such non-reactive materials include stainless steel, glass and the like. It is also contemplated that the interior of the reaction vessel can be passivated to make the interior surface less reactive. Passivation techniques are within the purview of those skilled in the art.

In embodiments, the reaction vessel may include any number of additional support means suitable for performing the methods described herein. Some non-limiting examples include a mixer, pressurizer, sprayer, heater, circulator, timer, computer, filter, waste lines, overflow tanks, sensors, and the like. In some embodiments, the reaction vessel is capable of heating the contents within the vessel. In embodiments, the reaction vessel may be placed in a separate heating device such as an oven to heat the monomer(s) and biodegradable polymeric material(s) contained therein.

The at least one monomer added to the reaction vessel may be any monomer capable of polymerizing via ring-opening polymerization. In embodiments, the at least one monomer may be a cyclic ester. Some examples of suitable cyclic esters include, but are not meant to be limited to, lactide, glycolide, p-dioxanone, $\epsilon$-caprolactone, methyl-tetrahydrofuran, $\omega$-pentadecalactone, $\omega$-dodecalactone, $\delta$-valerolactone, $\beta$-methyl-$\beta$-propiolactone, $\alpha$-methyl-$\beta$-propiolactone, $\gamma$-butyrolactone, trimethylene carbonate, tetramethylene carbonate, 2,2-dimethyl trimethylene carbonate and combinations thereof.

The biodegradable polymeric materials described herein include at least some amount of residual catalyst from when the biodegradable polymeric material was previously formed. The residual catalyst may be composed of at least one metal or metal compound selected from a group consisting of IA group, IIA group, IIB group, IVA group, IVB group, VA group and VIIA group in the periodic table.

Residual catalysts classified in the IA group, for example, include a hydroxide of alkali metal (such as, for example, sodium hydroxide, potassium hydroxide, and lithium hydroxide), a salt of alkali metal with weak acid (such as, for example, sodium lactate, sodium acetate, sodium carbonate, sodium octylate, sodium stearate, potassium lactate, potassium acetate, potassium carbonate, and potassium octylate), and an alkoxide of alkali metal (such as, for example, sodium methoxide, potassium methoxide, sodium ethoxide, and potassium ethoxide) and combinations thereof.

Other residual catalysts include those classified in the: IIA group, for example, a calcium salt of organic acids (such as, calcium acetate); IIB group, for example, a zinc salt of organic acid (such as, zinc acetate); IVA group, for example, tin powder may be mentioned as well as an organic tin type catalyst (such as, for example, monobutylin, tin lactate, tin octonoate, tin 2-ethylhexanoate, tin tartrate, tin dicaprylate, tin dilaurylate, tin diparmitate, tin distearate, tin dioleate, tin α-naphthoate, tin β-naphthoate, and tin octylate); IVB group, for example, a titanium type compound such as tetrapropyl titanate and a zirconium type compound such as zirconium isopropoxide; VA group, for example, an antimony type compound such as antimony trioxide; and, VIIA group, for example, a manganese salt of organic acid (such as, for example, manganese acetate).

All of these described above are conventionally known catalysts for ring-opening polymerization of suitable monomers, such as lactic acid. Among these, the catalyst composed of tin or stannous octoate may be of particularly useful in view of catalytic activity. Various combinations of catalysts, monomers, and polymeric materials may be utilized to for the coated biodegradable polymeric materials described herein.

The residual catalyst may represent from about 0.01% to about 5% by weight of the biodegradable polymeric material prior to being processed. In certain embodiments, the residual catalyst may represent from about 0.015% to about 3% by weight of the biodegradable polymeric material prior to being processed.

It is envisioned that after processing of the biodegradable polymeric material in the reaction vessel, the amount of residual catalyst is reduced. In some embodiments, the amount of the residual catalyst may be reduced by at least 10%. In other embodiments, the amount of residual catalyst may be reduced by at least 25%.

In some embodiments, the coated polymeric material may be catalyst free or contain no residual catalyst. In certain embodiments, the coated polymeric material may contain minimal traces of residual catalyst; in embodiments less than about 0.005% by weight; in some embodiments less than about 0.001% by weight.

The biodegradable polymeric material may include any polymeric material capable of being formed via ring-opening polymerization. Some non-limiting examples of suitable materials include at least one of poly-L-lactide, poly-DL-lactide, poly(lactic-co-glycolic acid), poly(glycolic acid), poly(p-dioxanone), poly(ε-caprolactone), poly(trimethylene carbonate), poly(tetramethylene carbonate), poly(hydroxylalkanoates), and combinations thereof.

Surface induced polymerization, as described herein, may be performed on biodegradable polymeric materials in any form. For example, the biodegradable material may be in the form of a biodegradable pellet, prior to further processing to form a finished product, such as a biodegradable implant or medical device. In other examples, the biodegradable material may be in the form of a finished product. Some examples of suitable products include sutures, staples, meshes, clips, screws, pins, rods, tacks, cables, occlusion devices, stents, and combinations thereof. In particularly useful embodiments, the biodegradable polymeric material is a fibrous material, such as monofilament, multifilament, suture, staple fiber, mesh, and the like.

The biodegradable polymeric materials and the at least one monomer may be positioned within the container for any suitable time necessary for the polymeric materials and the monomer to interact and form a coating on the polymeric material. In embodiments, the monomer(s) may have low melting points, i.e., below about 50° C., and the biodegradable polymeric materials may have a glass transition point slightly above the monomers melting point, i.e., above about 50° C. This combination makes ring-opening polymerization possible at lower temperatures and over longer periods of time.

In some embodiments, the biodegradable polymeric materials and the monomers may be heated in the container for periods of time ranging from about 30 seconds to about 10 days. In other embodiments, the biodegradable polymeric materials and the monomers may be heated in the container for periods of time ranging from about 1 hour to about 7 days. In still other embodiments, the biodegradable polymeric materials and the monomers may be heated in the container for periods of time ranging from about 4 hours to about 72 hours.

When heated, the monomer and/or polymeric material may be exposed to temperatures ranging from about 50° C. to about 100° C. In embodiments, the monomer and/or polymeric material may be exposed to temperatures ranging from about 60° C. to about 90° C. In certain embodiments, the temperature inside the vessel will be made higher than the temperature needed for the catalyst and the monomer to polymerize but below the temperature needed to further polymerize the polymeric material.

In some embodiments, the biodegradable polymeric materials and the monomers may be exposed to changes in pressure inside the container. For example, the pressure inside the container at anytime may be increased to enhance the interaction between the monomers and the polymeric materials. In another example, the container may include the polymeric material and prior to the introduction of the monomer into the container the pressure inside the container may be reduced to allow the polymeric material to expand slightly prior to the introduction of the monomer into the container thereby enhancing the perfusion of the monomer into the polymeric material. The pressure inside the container may range from about 0.1 to about 1 atm.

Methods wherein the coating of the biodegradable polymeric materials is performed at reduced temperatures, i.e., below the crystallization temperature may allow for blends of various materials on a particulate level which may prevent phase separation problems commonly associated with other coating, blending, and/or extruding processes.

The coated biodegradable polymeric materials, such as an implantable medical device, include a substrate formed from a biodegradable polymeric material which includes a reduced amount of residual catalyst. The coating is attached to at least a portion of the substrate via interpenetrating mechanisms through a surface of the substrate.

Figure 1B:
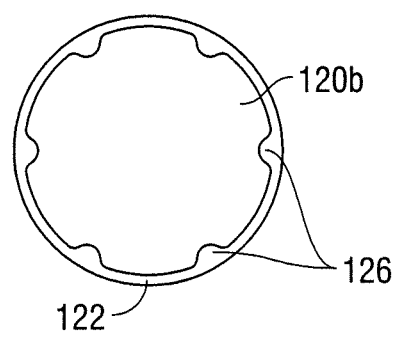
FIG. 1B shows a coated biodegradable polymeric material in accordance with one embodiment of the present disclosure.

Turning to FIG. 1A, biodegradable polymeric material 120a, i.e., a pellet, is shown prior to processing and including residual catalyst 130. Upon exposure to temperatures above the glass transition temperature of biodegradable polymeric material 120a, the polymeric material will soften and the polymer chains will have increased mobility thereby allowing the monomer and residual catalyst 130 to interact and form coating 122. As previously mentioned, the monomer may penetrate the surface of the polymeric materials or the increased mobility of the polymer chains may allow the residual catalyst to migrate to the surface to interact with the monomer. In FIG. 1B, biodegradable polymeric material 120b is shown after processing and includes coating 122 derived from monomers capable of ring-opening polymerization driven by residual catalyst 130. Coating 122 is attached or grafted to biodegradable polymeric material 120b along a surface of biodegradable polymeric material 120b. Biodegradable polymeric material 120b includes a reduced amount of residual catalyst 130.

In embodiments, the coated pellets of biodegradable polymeric material as described herein and shown in FIGS. 1A-1B may be further processed via an extrusion or molding process to form a finished product, such as an implantable medical device. Since the polymeric material and the coating are attached via the interpenetrating mechanisms, the blending of the two materials during an extrusion and/or molding process is less likely to phase separate. Thus the phase separation problems frequently associated with conventional polymer blends are avoided.

Figure 2A:
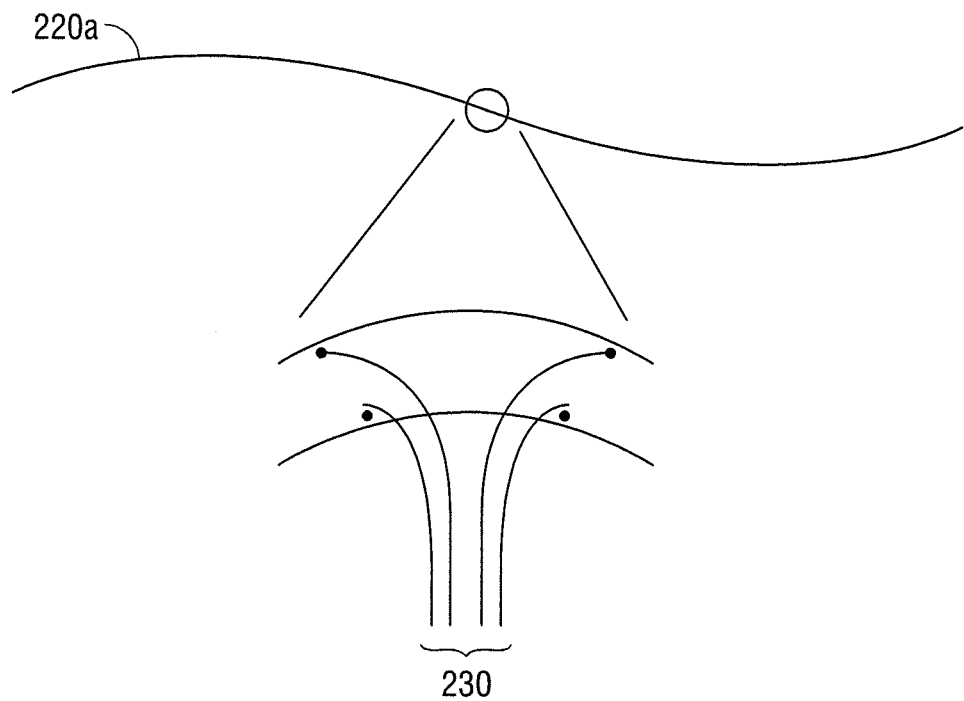
FIG. 2A shows a biodegradable polymeric material prior to the methods described herein.
Figure 2B:
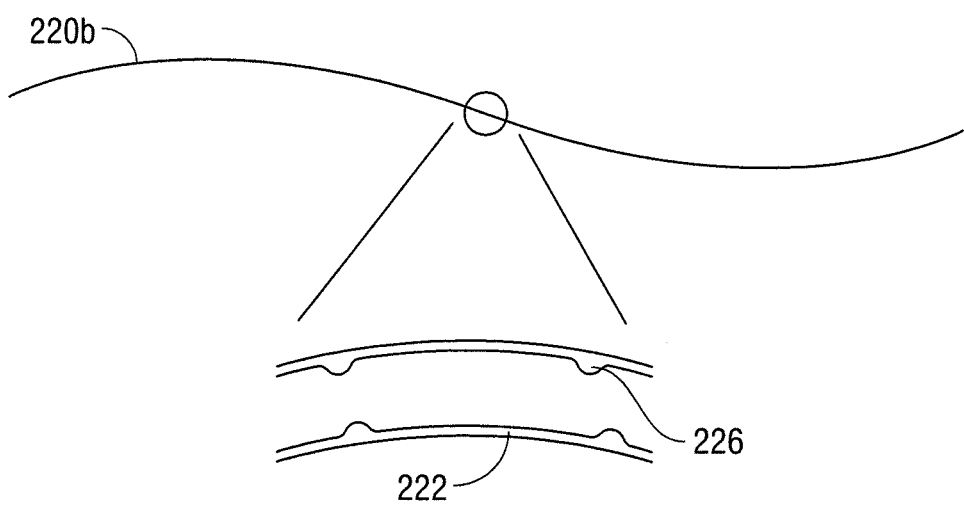
FIG. 2B shows a coated biodegradable polymeric material in accordance with another embodiment of the present disclosure.

As shown in FIG. 2A, biodegradable polymeric material 220a is an implantable medical device such as a suture. Biodegradable polymeric material 220a includes residual catalyst 230. Upon exposure to temperatures above the glass transition temperature of biodegradable polymeric material 220a, the polymeric material will soften and regions with a lower density may be created to allow the monomer and residual catalyst 230 to interact and form coating 222. In FIG. 2B, biodegradable polymeric material 220b is shown after processing and includes coating 222 derived from monomers capable of ring-opening polymerization driven by residual catalyst 230. Coating 222 is attached or grafted to biodegradable polymeric material 220b via interpenetrating mechanisms 226 along a surface of biodegradable polymeric material 220b. Biodegradable polymeric material 220b includes a reduced amount of residual catalyst 230.

Various combinations of monomers suitable for ring-opening polymerization and biodegradable polymeric materials may be utilized in the methods and devices described herein. The combinations may depend upon each materials different glass transition temperatures (Tg), and crystallization temperatures (Tc). It is envisioned that the biodegradable polymeric materials may be exposed to a temperature slightly above the glass transition temperature and below the crystallization temperature. It is further envisioned that the temperature to which the biodegradable polymeric material is exposed is sufficient for the polymerization of the monomer upon interaction with the residual catalyst.

Example 1

Pellets containing high-molecular weight biodegradable resins, such as Purasorb PL 38 and Purasorb PLD, each including about 0.005% by weight stannous octoate, are positioned within a container with a monomer such as p-dioxanone. The temperature is elevated to a between about 70-80° C. thereby softening the surface of the pellets and making the stannous octoate more accessible to the p-dioxanone monomer. At that temperature the p-dioxanone will begin to polymerize following interaction with the stannous octoate along the surface of the pellets creating a surface coating grafted to the pellet. The pellets remain heated for about 24 hours. Upon removal from the heat and/or container, the coated pellets include about 0.001% by weight stannous octoate which is less than prior to processing.

Example 2

Filaments made from Purasorb PL 38 and Purasorb PLD and containing about 0.005% by weight stannous octoate, are positioned within a container with a monomer such as p-dioxanone. The temperature is elevated to a between about 70-80° C. thereby softening the surface of the filaments and making the stannous octoate more accessible to the p-dioxanone monomer. At that temperature the p-dioxanone will begin to polymerize following interaction with the stannous octoate along the surface of the filaments creating a surface coating grafted to the filaments. The filaments remain heated for about 8 hours. Upon removal from the heat and/or container, the coated filaments include about 0.003% by weight stannous octoate which is less than prior to processing. In addition, a poly-dioxanone coating is attached to the surface of the filaments It will be understood that various modifications may be made to the embodiments disclosed herein. Thus, those skilled in the art will envision other modifications within the scope and spirit of the claims.

What is claimed is:

1. An implantable medical device comprising:
   a substrate comprising a biodegradable polymeric material capable of being formed via ring-opening polymerization and containing a reduced amount of residual catalyst; and
   a biodegradable coating positioned on at least a portion of the substrate, wherein the biodegradable coating is derived from at least one monomer capable of ring-opening polymerization by the residual catalyst contained in the biodegradable polymeric material.

2. The implantable medical device of claim 1 wherein the implantable medical device is selected from the group consisting of sutures, staples, meshes, clips, screws, pins, rods, tacks, cables, occlusion devices, stents, and combinations thereof.

3. The implantable medical device of claim 1 wherein the implantable medical device is a suture.

4. The implantable medical device of claim 1 wherein the residual catalyst comprises at least one metal or metal compound selected from a group consisting of IA group, IIA group, IIB group, IVA group, IVB group, VA group and VIIA group in the periodic table.

5. The implantable medical device of claim 1 wherein the residual catalyst comprises stannous octoate.

6. The implantable medical device of claim 1 wherein the reduced amount of residual catalyst is less than about 0.005% by weight of the biodegradable polymeric material.

7. The implantable medical device of claim 1 wherein the reduced amount of residual catalyst is less than about 0.001% by weight of the biodegradable polymeric material.

8. The implantable medical device of claim 1 wherein the at least one monomer comprises a cyclic ester.

9. The implantable medical device of claim 8 wherein the cyclic ester comprises an aliphatic cyclic ester.

10. The implantable medical device of claim 8 wherein the cyclic ester is selected from the group consisting of lactide, glycolide, p-dioxanone, ε-caprolactone, methyl-tetrahydrofuran, ω-pentadecalactone, ω-dodecalactone, δ-valerolactone, β-methyl-β-propiolactone, a-methyl-β-propiolactone, γ-butyrolactone, trimethylene carbonate, tetramethylene carbonate, 2,2-dimethyl trimethylene carbonate and combinations thereof.

11. The implantable medical device of claim 1 wherein the monomer is ε-caprolactone and the substrate includes polylactide.

12. The implantable medical device of claim 1 wherein the monomer has a melting temperature below about 50° C. and the substrate includes a material having a glass transition temperature greater than about 50° C.

13. The implantable medical device of claim 1 wherein the substrate includes a biodegradable polymeric material selected from the group consisting of poly-L-lactide, poly-DL-lactide, poly(lactic-co-glycolic acid), poly(glycolic acid), poly(p-dioxanone), poly(ε-caprolactone), poly(trimethylene carbonate), poly(tetramethylene carbonate), poly(hydroxylalkanoates), and combinations thereof.

14. The implantable medical device of claim 1 wherein the biodegradable coating is continuous along the surface of the substrate.

15. The implantable medical device of claim 1 wherein the biodegradable coating is discontinuous along the surface of the substrate.

16. A method of inducing ring-opening polymerization of a cyclic ester monomer on a surface of a medical device comprising:
   providing a closed container which includes a cyclic ester monomer capable of ring-opening polymerization and medical device comprising a biodegradable polymeric material capable of being formed via ring-opening polymerization and including a residual catalyst; and
   heating the closed container to at least a glass transition temperature of the biodegradable polymeric material of the medical device and below the crystallization temperature of the biodegradable polymeric material of the medical device to induce ring-opening polymerization of the cyclic ester monomer with the residual catalyst contained in the biodegradable polymeric material.

17. A method of grafting a biodegradable coating onto a surface of a biodegradable polymeric material comprising:
   providing a container which includes at least one monomer capable of polymerizing via cationic ring-opening polymerization and a pellet of a biodegradable polymeric material capable of being formed via ring-opening polymerization and containing a residual catalyst;
   placing the container with the pellet of biodegradable polymeric material in an oven for a period of time, wherein the oven is heated above the glass transition temperature and below the crystallization temperature of the biodegradable polymeric material;
   polymerizing the monomer with the residual catalyst contained in the biodegradable polymeric material to form a coated pellet; and,
   processing the coated pellet to form an implantable medical device.

18. The implantable medical device of claim 1 wherein the implantable medical device is a mesh.

19. The implantable medical device of claim 1 wherein the biodegradable coating is grafted via interpenetrating mechanisms through a surface of the substrate.

* * * * *